United States Patent [19]

Lee

[11] Patent Number: 4,726,768
[45] Date of Patent: Feb. 23, 1988

[54] PLASTER DAM FOR MOUNTING DENTAL CASTS

[76] Inventor: Robert L. Lee, 22575 Barton Rd., Grand Terrace, Colton, Calif. 92324

[21] Appl. No.: 913,730

[22] Filed: Sep. 30, 1986

[51] Int. Cl.[4] ............................................. A61C 19/00
[52] U.S. Cl. ........................................ 433/34; 433/40; 433/68; 433/213
[58] Field of Search .................. 433/60, 34, 213, 38, 433/39, 40, 48

[56] References Cited

U.S. PATENT DOCUMENTS

| | | | |
|---|---|---|---|
| 270,566 | 1/1883 | Graves | 433/213 |
| 538,204 | 4/1895 | Traphagen | 433/41 |
| 2,621,407 | 12/1952 | Schlesinger | 433/60 |
| 2,835,628 | 5/1958 | Saffir | 433/39 |
| 3,082,531 | 3/1963 | Jacobson | 433/39 |
| 3,360,860 | 1/1968 | Roland | 433/45 |
| 4,449,931 | 5/1984 | Saito | 433/34 |
| 4,600,385 | 7/1986 | Lee | 433/60 |

FOREIGN PATENT DOCUMENTS 2920521 12/1980 Fed. Rep. of Germany ........ 433/60
377480 5/1964 Switzerland ........................ 433/39

Primary Examiner—John J. Wilson
Attorney, Agent, or Firm—Knobbe, Martens, Olson & Bear

[57] ABSTRACT

A strip of stiff paper is wrapped around the edge of a dental cast mounting plate of a dental articulator to serve as a dam for confining moist plaster used for mounting a dental cast to the plate. After the plaster has hardened, the strip may be readily removed, leaving a clean, easily observable edge between the plaster and the plate, which is very helpful in the use of interchangeable plates with dental casts as well as use with the dental "split-cast" mounting plate technique.

2 Claims, 6 Drawing Figures

PLASTER DAM FOR MOUNTING DENTAL CASTS

FIELD OF THE INVENTION

This invention relates to the field of dental articulators, and more particularly to an improved system for securing a dental cast to a dental cast mounting plate of a dental articulator.

BACKGROUND OF THE INVENTION

The upper and lower frames of a dental articulator normally include dental cast mounting plates to which are attached dental casts of a patient's upper and lower teeth or gums. In the attachment process, the casts are held in a desired predetermined position by suitable apparatus and they are then attached to the dental cast mounting plates on the articulator by soft plaster. After the plaster has hardened, the mounting apparatus is removed and the dental casts are then properly held by the plaster to the articulator frames, thus enabling the articulator frames to be hinged and manipulated in a desired manner to simulate jaw movements.

Dental cast mounting plates have been made in a variety of shapes and configurations. Mostly, they have been relatively flat plates with one or more upwardly extending projections to facilitate attachment to the plaster to the plate. The moist plaster typically has a consistency similar to that of whipped cream or shaving creams such that the plaster tends to stay somewhat where it is placed, but usually a certain amount of plaster flows or squeezes outwardly beyond the periphery of the dental cast and the mounting plate. Since the consistency of the plaster varies the amount of the wet plaster squeezed from beneath the plate and the cast varies. However, in almost all instances some clean-up is required to remove this excess material. Some of this clean-up can occur while the plaster is still soft, but the remainder must be completed by scraping and sanding after the material has hardened, which requires time as well as some skill and patience and may also damage the edges of the mounting plate.

In an attempt to alleviate this problem, some dental cast mounting plates include a short outer wall to confine the soft plaster. One example of this is shown in U.S. Pat. No. 4,600,385. While such wall is of assistance, in placing the soft plaster, it is more difficult to removed hardened plaster from the outer edges of plates having the fixed outer wall. Further, there are "split-cast" mounting plates as shown in this patent application, designed to be viewed from the side with a dental cast mounted thereon, so that the interface between the mounting p late and the cast can be observed to check the alignment and accuracy of the original mounting and cast replacement operation. A fixed outer wall on such mounting plates would interfere with this inter face viewing. Use of this "split-cast" type of plate therefore requires particular care in removal of excess plaster to facilitate such observations. Also, there is danger of damaging such a plate while scraping or sanding away the hardened plaster. This damage or change in the plate surfaces also creates inaccuracies in reuse.

Accordingly a need exist for an improved system for mounting dental casts to mounting plates on a dental articulator.

SUMMARY OF THE INVENTION

In accordance with the structure of the invention, there is provided a thin element made of stiff but formable material, such as paper or plastic or this metal, which surrounds the periphery of a dental cast mounting plate for a dental articulator. The height of the element is sufficient to provide a form or dam for plaster to be applied to the plate. In a preferred form of the invention, the element is initially in the shape of a flat, elongated strip. The length of the strip or element is greater than the peripheral distance of the portion of the mounting plate to be enclosed, and adhesive is provided on each end of the strip. Thus, in accordance with one aspect of the method of the invention, one end of the strip is attached to the edge of the mounting plate, and the strip is wrapped around the periphery of plate so that the then second end of the strip overlaps the first and is secured thereto by the adhesive on the second end.

Once the plaster has hardened, the dam may be easily cut or otherwise broken and removed, thereby exposing the clear interface edge of the plate and the edge of the plaster joining the plate. No cleaning scraping or sanding of this exposed edge is required.

In accordance with another aspect of the invention, the strip may be provided with suitable lines or other indicia to mark the line at which the second end of the strip is to be secured to the first. This allows the strip to be conveniently formed into a loop of the desired size before it is positioned on the plate. It is then an easy matter to slip one of the loops over the plate to form the desired dam. The loop can be also formed directly without being in strip from and having overlapping ends.

Some additional advantages of this system are that the strips are easy to apply, easy to remove and are inexpensive. The strips save the valuable time of the dentist or his assistants; and the resulting mounting surface of the dental casts are easily observed, thus providing greater precision in the use of an articulator.

DETAILED DESCRIPTION OF PREFERRED EMBODIMENT

Figure 1:
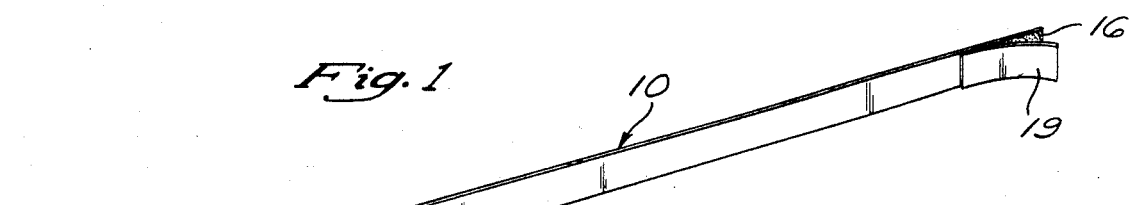
FIG. 1 is a perspective view of the strip like element of the invention.
Figure 2:
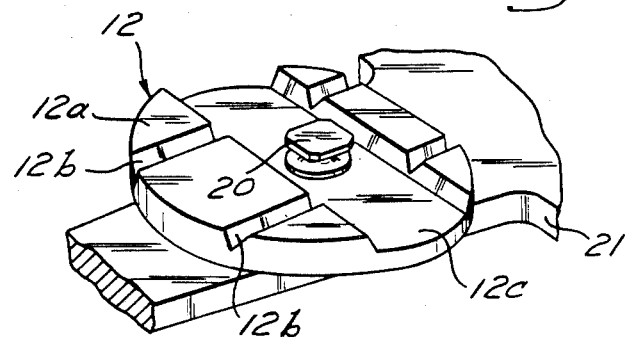
FIG. 2 is a perspective view of a dental cast mounting plate and a portion of an articulator frame.

Referring to FIGS. 1 and 2, the forming element 10 of the invention has an elongated strip like configuration of thin, but relatively stiff material, such as sturdy paper or plastic. If paper is used it must be able to withstand being in contact with moist plaster without losing its strength. Thus, at least the inner surface should be water resistant or repellant. The element may be made of whatever length is needed to wrap around a particular dental cast mounting plate 12, but is typically about 6 inches long. Similarly the height of the strip may be made as necessary to confine soft plaster, but is preferably about ½ inch high.

A strong, contact-type adhesive 14 and 16 is preferably provided on the inner surface of each end of the strip, and each of these adhesvie areas is initially preferably covered with a removable protective tab 18 and 19.

The dental cast mounting plate 12 shown in FIG. 2 has a generally flat upper surface 12a having a pair of spaced grooves 12b formed therein, with such grooves having a V-shaped cross-section. The upper surface of the plate further has a transversely extending channel 12c intersecting the grooves 12b. The plate is shown attached to one frame 21 of a dental articulator by a knob 20 which extends upwardly in the channel 12c. The undercut on the knob is useful for properly securing plaster to the plate, in that the moist plaster applied to the plate extends beneath the upper portion of the knob. While various arrangements may be used for attaching the plate and the knob to the articulator frame 21, a preferred arrangement is illustrated in U.S. Pat. No. 4,600,385. In that arrangement, the knob is internally threaded and attached by a screw (not shown) that extends through the articulator frame and upwardly into the knob. With this arrangement, the screw can be unthreaded from the knob and the hardened plaster with the knob embedded therein can be removed from the mounting plate to enable the mounting plate to be reused. The above-referenced patent also illustrates additional portions of a dental articulator.

Figure 3:
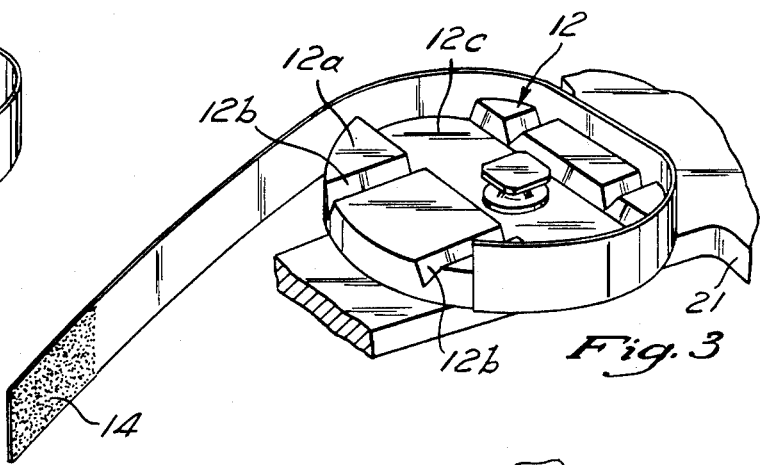
FIG. 3 is a perspective view of the strip of FIG. 1 partially installed on a dental plate.
Figure 4:
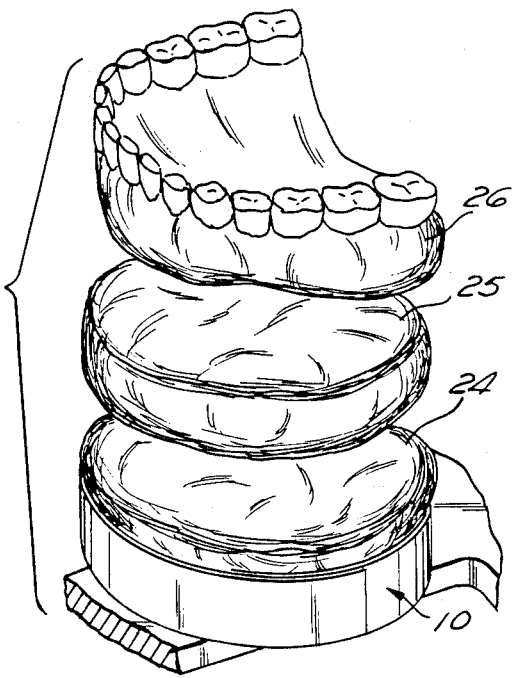
FIG. 4 is a perspective view of the strip fully installed on a dental mounting plate and in use confining plaster about to be joined to a dental cast.

In the primary method of the invention, the adhesive protective tab 19 on one end of the strip is removed and the adhesive 16 on that end is pressed against the edge of the plate 12 and wrapped around the plate to the position shown in FIG. 3. The tab 18 on the trailing end is then removed, exposing the adhesive 14. The wrap is completed by having the trailing end of the strip overlap the attached end to form a loop and attached to the first end of the strip by the adhesive 14, as shown in FIG. 4. Note that the height of the strip is considerably greater than the thickness of the plate such that the strip extends upwardly to form a dam for plaster to be applied to the plate.

In use, a quantity of soft plaster 24 is positioned on the plate in sufficient amount to make certain that all portions of the plate upper surface are amply covered. Also, plaster is pressed all around the knob 20, including the undercut portion. The loop or dam 10 conveniently confines the plaster in this operation. A quantity of plaster 25 is also applied to the backside of a previously-made dental cast 26, while it is supported in a predetermined, desired position by suitable apparatus (not shown). The plastered surfaces are then pressed together, and the plaster allowed to set and harden, to thereby join the dental cast with the mounting plate.

For simplicity purposes, the dental cast 26 is shown positioned above the mounting plate in FIG. 4 about to be joined to the plate; however, the usual procedure is somewhat more involved. For example, the support apparatus for the dental cast is usually mounted on or referenced to a second frame (not shown) of a dental articulator, which is hinged to the frame 21 of the articulator supporting the plate 12. The hinged frames at that stage are normally in the fully opened, or 180°, orientation. The dental cast is normally supported in a position inverted from that shown in FIG. 4, that is, with the crowns of the teeth facing downwardly to engage the support apparatus. After the quantity of plaster 24 has been applied to the plate 12 and the quantity 25 on the backside of the dental cast, the articulator frame 21 carrying the mounting plate is then swung 180° into the fully closed position wherein the soft plaster 24 on the plate is pressed against the soft plaster 25 on the cast. Thus, at that stage the components are actually inverted from that shown in FIG. 4. During this operation, the loop 10 continues to confine the plaster 24 around the periphery of the plate so that the plaster in that area does not squeeze outwardly.

The periphery of the plaster connection to the dental cast is not critical, and normally only enough plaster is used on the dental cast to ensure a good connection. Frequently, to present a more finished appearance, additional plaster is applied to the joined cast and plate in the area of the cast after the initial plaster is hardened.

After hardening of the plaster, the dam-forming element 10 may be removed from the mounting plate 12 by manually gripping the outer end of the strip, pulling it away from its adhesive connection, and unwrapping the rest of the strip from the plate. Alternatively, a tool may be employed to cut the strip at any location to remove it, in that the strip will normally be discarded after a single use.

Figure 5:
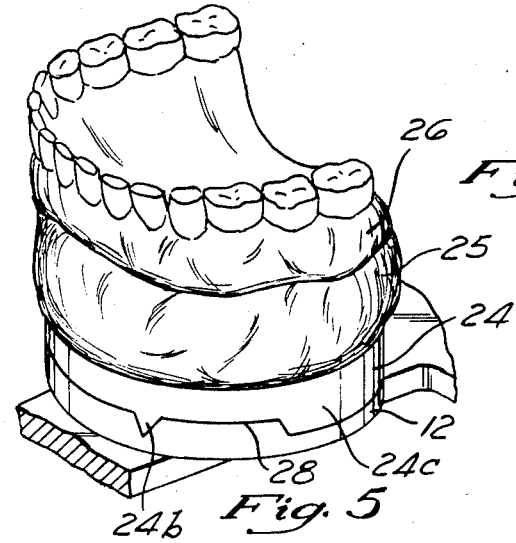
FIG. 5 is a perspective view of a mounted cast after the forming strip has been removed.

This leaves the edge of the mounting plate and the joining plaster surface clean and smooth, without any scraping or sanding, as shown in FIG. 5. The intersection 28 between the plaster 24 and the cast 12 is clear and sharp and readily observed. Thus, the operator can be assured that the interconnection and re connection of removed casts is proper.

Normally, a second dental cast of the person's other jaw is then similarly attached to a second mounting plate on the other frame (not shown) of a dental articulator. In this operation, the teeth of the two dental casts are properly mated, usually through the use of an alignment member having impression of the teeth in a known position, and the second dental cast is plastered to a second mounting plate in this aligned position. The plaster is confined by utilizing a second strip 10 on the second mounting plate in the manner described above.

As mentioned above, it is desirable that the dental cast, together with its attached plaster be removable from a dental cast mounting plate so that the mounting plate can be used with other dental casts. A suitable release material is typically sprayed on the plate before the plaster is applied. This helps the later separation of the hardened plaster from the plate. As explained, separation is accomplished by removing a mounting screw that threads into the knob 20 embedded in the plaster, and this enables the cast together with the plaster and the knob to be removed as a unit.

The alignment grooves and the alignment channel 12c in the upper face of the mounting plate, shown in FIGS. 2 and 3, are precisely formed. Thus, when a dental cast and its attached plaster is to be remounted on a different but identical mounting plate, the ribs 24b and projection 24c in the lower surface of the plaster, shown in FIG. 5, should fit precisely with the mating alignment grooves 12b and alignment channel 12c in a different mounting plate. The smooth exposed edges of the mounting plate and the plaster on the mating dental cast can be easily observed to make certain that the alignment is proper.

In mounting a dental cast to a different plate, a small particle of plaster or other material could be on the surface of the mounting or the plaster, thus preventing the plaster from accurately mating with the mounting plate. This imperfection can be readily detected since the edges of the plate and the plaster are observable. It is, of course, very important that the interconnection be perfect in that the relationship between the mating surfaces of the teeth will be altered if the connection to the mounting plates is not precise. Thus, the importance and convenience of the forming strips or dams 10 can be readily appreciated.

Figure 6:
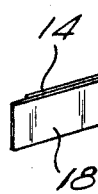
FIG. 6 is a perspective view of the strip in loop form.
Figure 6:
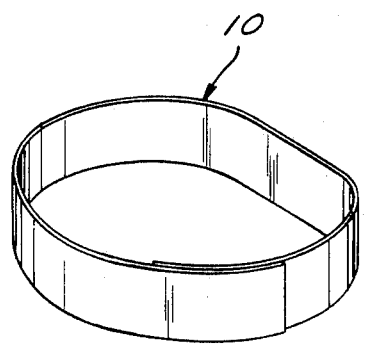

Providing the dam element 10 in strip form as illustrated in FIGS. 1 and 3 is convenient and practical in that the dental cast mounting plates currently on the market have different peripheral dimensions, and future designs will undoubtedly also include variations. With the strip of FIG. 1, it is easy to form the desired loop shape that fits snuggly around the mounting plate. Once the desired size is known, the strip can be formed into the desired loop size before being mounted on the mounting plate as illustrated in FIG. 6. Once formed, the loop can simply be slipped over the top of the plate. To facilitate forming the loops before mounting on a plate, the exterior of the strip may be provided with suitable lines 30 or other indicia to serve as a guide where the overlapping end of the strip should be situated when the loop is formed. Of course, loops of a desired size may be directly formed without being first made in strip form as shown in FIG. 1. Thus, there would be no need for adhesive on the ends of the strip in that there would be no overlappng ends, as in FIG. 6.

What is claimed is:

1. A forming element for use in connection with applying plaster to a dental cast mounting plate of a dental articulator, said element comprising a thin, flat, elongated strip of stiff material that is sufficiently flexible and formable that it can be wrapped around and conformed to the perimeter of said plate, an adhesive area on one end of said strip for attaching said end to said plate, a removable protective tab covering said adhesive area, the length of said strip being greater than the perimeter of the plate so that the other end of said strip overlaps said one end, an adhesive area on said strip other end for attaching said other end to an overlapped portion of the strip to thereby form a loop surrounding the plate, a removable protective tab initially covering the adhesive area on said other end, the height of said loop being considerably higher than the height of the exterior of said plate so that the loop is adapted to form a dam for soft plaster applied to said plate, the surface of said loop to be engaged by said moist plaster being sufficiently water resistant or water-repellant so as not to lose its strength or stiffness while it is confining the plaster, and the interior of said loop being adapted to be readily separated from said plate and said plaster after the plaster has hardened.

2. A method of attaching a dental cast to a dental cast mounting plate comprising the steps of removing a protective tab from an adhesive area on one end of a then, elongated strip that is stiff but sufficiently flexible and formable such that it can be wrapped around the perimeter of the plate, attaching said one end of the strip to the edge of said plate by pressing the adhesive area against the plate, wrapping the strip around the plate with the lower portion of the strip engaging the plate and the upper portion of the strip extending above the perimeter of the plate, removing a protective tab on the other end of said strip, overlapping said one end of the strip with said other end, and pressing an adhesive area on said other end of the strip against an overlapped portion of said strip to thereby complete a loop dam around the perimeter of the plate, applying moist plaster to said plate, with the plaster being outwardly confined by said loop, positioning a dental cast onto said moist plaster, and removing said loop after said plaster has hardened, to thereby expose the edge of said plate free of plaster.

* * * * *